United States Patent [19]
Ohuchi et al.

[11] Patent Number: 5,733,917
[45] Date of Patent: Mar. 31, 1998

[54] HETEROCYCLIC COMPOUND

[75] Inventors: Yutaka Ohuchi; Masaji Suzuki; Hajime Asanuma; Sadakazu Yokomori; Katsuo Hatayama; Yoshihiko Isobe; Haruko Kijima; Makoto Muramatsu, all of Tokyo, Japan

[73] Assignee: Taisho Pharmaceutical Co., Ltd., Tokyo, Japan

[21] Appl. No.: 701,000

[22] Filed: Aug. 21, 1996

Related U.S. Application Data

[63] Continuation of PCT/JP95/00228 Feb. 17, 1995.

[30] Foreign Application Priority Data

Feb. 28, 1994 [JP] Japan ................. 6-030119

[51] Int. Cl.$^6$ .......... A61K 31/46; A61K 31/47; C07D 451/06; C07D 451/04
[52] U.S. Cl. .......... 514/299; 514/304; 546/112; 546/126
[58] Field of Search ............... 546/112, 126; 514/299, 304

[56] References Cited

U.S. PATENT DOCUMENTS

| | | | |
|---|---|---|---|
| 5,106,851 | 4/1992 | Turconib et al. | 514/259 |
| 5,248,684 | 9/1993 | Suzuki et al. | 514/299 |

FOREIGN PATENT DOCUMENTS

| | | |
|---|---|---|
| 382 687 | 8/1990 | European Pat. Off. |
| 458 636 | 11/1991 | European Pat. Off. |

OTHER PUBLICATIONS

Talley, N.J., Review Article: 5-hydroxytryptamine agonists . . . , Alimentary Pharmacology & Therapeutics, vol. 6, p. 273, 1992.

Dumis, Aline, et al, A Nonclassical 5-Hydroxytryptamine Receptor . . . , Molecular Pharmacology, vol. 34, p. 880, 1988.

Molecular Pharmacology, 34: 880–887, 1988, A Nonclassical 5-Hydroxytryptamine Receptor Positively Coupled with Adenylate Cyclase in the Central Nervous System, Aline Dumuis et al.

Aliment. Pharmacol. Ther. (1992) 6, 273–289, Review Article: 5-Hydroxytryptamine Agonists and Antagonists in the Modulation of Gastrointestinal Motility and Sensation: Clinical Implications, N.J. Talley.

*Primary Examiner*—Yogendra N. Gupta
*Assistant Examiner*—Sabiha N. Qazi
*Attorney, Agent, or Firm*—Cushman Darby & Cushman IP Group of Pillsbury Madison & Sutro LLP

[57] ABSTRACT

Endo-(8-methyl-8-azabicyclo[3.2.1]oct-3-yl) 1-isopropyl-2 (1H)-quinolone-3-carboxylate represented by Formula (I):

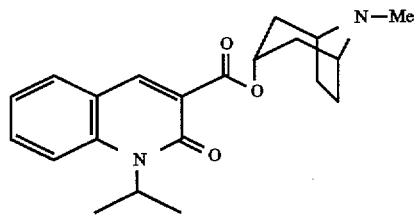

or an acid addition salt thereof acts on a serotonin 4 receptor thereby to have a serotonin-like receptor stimulating activity, therefore has an action on activating gastrointestinal motor functions and thus is effective for the improvement of gastrointestinal conditions such as heartburn, anorexia, bowel pain or abdominal distension accompanied by chronic gastritis or postoperative gastroparesis, and further for the treatment of gastro-esophagal reflux, intestinal pseudo-obstruction or constipation.

6 Claims, No Drawings

HETEROCYCLIC COMPOUND

CROSS-REFERENCE TO RELATED APPLICATION

This application is a continuation application of PCT/JP95/00228 filed on Feb. 17, 1995 designating U.S., all the content of which is incorporated herein by reference.

TECHNICAL FIELD

The present invention relates to a heterocyclic derivative and a pharmaceutical use thereof, and more particularly, the present invention relates to a novel heterocyclic derivative or a pharmaceutically acceptable salt thereof having a stimulating action on a serotonin 4 receptor and a pharmaceutical use thereof.

BACKGROUND ART

Serotonin is a neurotransmitter which is widely distributed in a living body and has a remarkable variety of physiological activities. Dumuis A et al reported in 1988 that the serotonin 4 receptor exists besides known three subtypes of the serotonin 1 receptor, serotonin 2 receptor and serotonin 3 receptor (Molecular Pharmacology, vol. 34, page 880, 1988).

Serotonin 4 receptors are considered to take a part in contraction of ileum or ascending colon of guinea pig or relaxation of rat esophagus. Cisapride and renzapride, which are stimulants of serotonin 4 receptors, accelerate gastrointestinal motor functions and thus are considered to be effective for the improvement of gastrointestinal conditions such as heartburn, anorexia, bowel pain or abdominal distension accompanied by chronic gastritis or postoperative gastroparesis, and further for the treatment of gastroesophagal reflux, intestinal pseudo-obstruction or constipation (Alimentary Pharmacology and Therapeutics, vol. 6, page 273, 1992).

Japanese Patent Kokai No. 4-226980 discloses quinolone derivatives having an antagonizing action on a serotonin 3 receptor as heterocyclic compounds having an antagonizing action or stimulating action on serotonin receptors.

On the other hand, Japanese patent Kokai No. 3-197462 discloses quinazolinecarboxylic acid derivatives. The heterocyclic compounds are those having an affinity to muscarinic receptors, but are unknown about any activity on serotonin 4 receptors.

As stated above, no research has been reported on any heterocyclic compounds having an excellent antagonizing or stimulating action particularly on serotonin 4 receptors.

An object of the present invention is to provide a novel heterocyclic compound having a stimulating action on a serotonin 4 receptor and a pharmaceutical use thereof.

DISCLOSURE OF THE INVENTION

The present invention relates to endo-(8-methyl-8-azabicyclo[3.2.1]oct-3-yl) 1-isopropyl-2(1H)-quinolone-3-carboxylate represented by Formula (I):

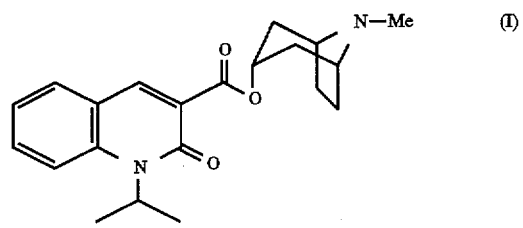

or a pharmaceutically acceptable salt thereof.

Further, the present invention relates to the above-mentioned compound or a pharmaceutically acceptable salt thereof for use as an effective ingredient of a pharmaceutical composition.

Furthermore, the present invention relates to a pharmaceutical composition for stimulating a serotonin 4 receptor comprising as an effective ingredient the above-mentioned compound or a pharmaceutically acceptable salt thereof.

Still furthermore, the present invention relates to a method for stimulating a serotonin 4 receptor which comprises administering to mammals containing human a pharmacologically effective amount of the above-mentioned compound or a pharmaceutically acceptable salt thereof.

In addition, the present invention relates to use of the above-mentioned compound or a pharmaceutically acceptable salt thereof for the manufacture of a pharmaceutical composition for stimulating a serotonin 4 receptor.

BEST MODE FOR CARRYING OUT THE INVENTION

The pharmaceutically acceptable salts of the compound of Formula (I) of the present invention are acid addition salts, for examples, a salt with a mineral acid such as hydrochloric acid, hydrobromic acid, hydroiodic acid, sulfuric acid, nitric acid or phosphoric acid; a salt with an organic acid such as acetic acid, oxalic acid, citric acid, tartaric acid, maleic acid, succinic acid, fumaric acid, benzenesulfonic acid, p-toluenesulfonic acid or methanesulfonic acid.

The compound of Formula (I) of the present invention (hereinafter sometimes referred to as "Compound (1)") can be prepared, for example, according to the following methods.

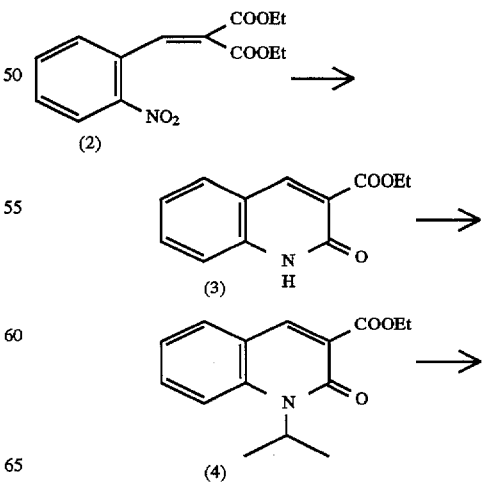

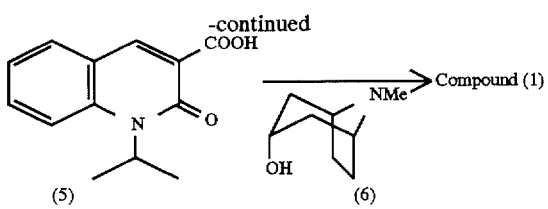

Compound (2) of a starting material can be prepared by the method described in J. Chem. Soc., page 3462, 1960.

Reductive ring closure of from Compound (2) to Compound (3) can be carried out under conventional reaction conditions for reduction of a nitro group. The reaction permits reduction and ring closure simultaneously to obtain Compound (3). Examples of the reduction conditions are ① catalytic reduction in an appropriate solvent using palladium-carbon or platinum and ② reduction in an appropriate inert solvent using iron or tin, or using sodium sulfide-ammonium chloride.

Examples of the solvent to be used in the reduction of ① are water, acetic acid, an alcohol, a hydrocarbon (e.g. hexane), an ether (e.g. diethyl ether or tetrahydrofuran), a non-protic polar solvent (e.g. N,N-dimethylformamide) and a solvent mixture thereof. Examples of the solvent to be used in the reduction of ② are water, acetic acid, methanol, ethanol, dioxane and a solvent mixture thereof.

The reaction temperatures for the reductions in ① and ② are usually from 0° C. to the boiling point of the solvent. The reaction times are each appropriately from 30 minutes to 12 hours, in usual.

N-Isopropylation of from Compound (3) to Compound (4) can be carried out under conventional conditions for N-alkylation of an acid amide, for example, a reactive derivative for introduction of an isopropyl group can be reacted with Compound (3) in an appropriate solvent in the presence of a base. Examples of the base to be used in the appropriate solvent are an alkali metal (e.g. sodium or potassium), an alkali hydride (e.g. sodium hydride), an alkali alkoxide (e.g. sodium ethoxide or potassium tert-butoxide), an alkali hydroxide (e.g. sodium hydroxide or potassium hydroxide), a carbonate (e.g. sodium carbonate or potassium carbonate) and an amine (e.g. triethylamine or pyridine).

Examples of the solvent to be used are water, an alcohol (e.g. methanol or ethanol), an ether (e.g. diethyl ether, dioxane or tetrahydrofuran), a hydrocarbon (e.g. hexane or benzene), a non-protic polar solvent (e.g. N,N-dimethylformamide) or a solvent mixture thereof. The reaction temperature is usually from 0° C. to the boiling point of the solvent.

The reaction time is appropriately from 30 minutes to 12 hours, in usual.

Examples of the reactive derivative for introduction of an isopropyl group are isopropyl halides such as isopropyl iodide.

Hydrolysis of from Compound (4) to Compound (5) can be carried out under conventional conditions for hydrolysis. For example, an acidic hydrolysis using hydrochloric acid or acetic acid or a basic hydrolysis using sodium hydroxide can be applied. The reaction temperature is usually from 0° C. to the boiling point of the solvent. The reaction time is appropriately from 30 minutes to 12 hours, in usual.

Esterification of from Compound (5) to Compound (1) can be carried out by a reaction of Compound (5) or a reactive derivative thereof with tropine (Compound (6)) to give Compound (1).

This esterification may be carried out by a known method in the art per se.

Examples of the esterification are a reaction of a reactive derivative of Compound (5) (e.g. an acid halide, a lower alkyl ester, or an activated ester, an imidazolide or a mixed acid anhydride thereof) with Compound (6) and a direct binding of Compound (5) with Compound (6) using a condensing agent.

When the acid halide is used, a halide of Compound (5) is reacted with Compound (6) in a reaction-inert solvent in the absence or presence of a base usually at 0° C. to the boiling point of the solvent.

Examples of the solvent are ether, tetrahydrofuran, dioxane, methylene chloride, chloroform, dichloroethane, benzene, toluene, xylene, water and a mixture thereof.

Examples of the base are sodium carbonate, sodium hydroxide, potassium hydroxide, pyridine, triethylamine, N,N-dimethylaniline, sodium hydride and n-butyl lithium.

The reaction time is appropriately from 30 minutes to 12 hours, in usual.

When the direct binding is applied using the condensing agent, Compound (5) is reacted with Compound (6) in a reaction-inert solvent in the presence of the condensing agent, usually at 0° C. to the boiling point of the solvent.

Examples of the solvent to be used are those described above.

Examples of the condensing agent to be used are dicyclohexylcarbodiimide, 2-chloro-N-methylpyridinium iodide and diphenylphosphoryl azide.

Compound (4) or (5) in the above-mentioned preparation method may be also prepared according to the following preparation scheme described below:

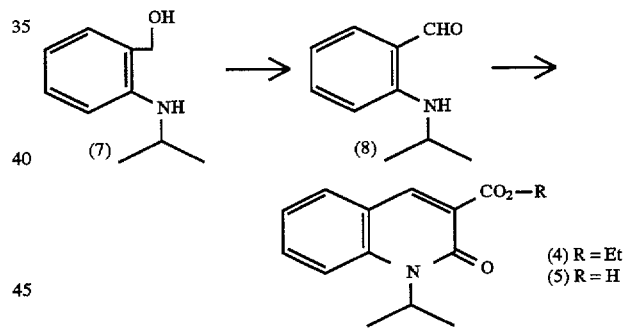

Oxidation of from Compound (7) to Compound (8) may be carried out under known oxidation conditions, for example, by using a transition metal compound (e.g. manganese dioxide or chromic acid), an organic compound (e.g. DMSO, chloranil or DDQ), lead acetate or selenium dioxide.

Examples of the solvent to be used are dioxane, tetrahydrofuran, ether, benzene, toluene, chloroform, water and a mixture thereof. The reaction temperature is appropriately from −20° C. to the boiling point of the solvent, in usual. The reaction time is appropriately from 30 minutes to 24 hours, in usual.

Compound (8) may be also used in the form of an acid addition salt such as hydrochloride.

Compound (8) is condensed with malonic acid or a malonic acid ester in the presence or absence of a condensing agent to convert into Compound (4) or (5).

Examples of the condensing agent to be used are a hydroxide, a carbonate, a bicarbonate, an alcoholate and an amide of an alkali metal; ammonia, an amine (e.g. piperidine), acetic acid, acetic anhydride and zinc chloride. These condensing agents can be used alone or in admixture.

The compound of the present invention can be prepared using Compound (4) or (5) in a manner similar to that described as above.

Compound (1) of the present invention acts on a serotonin 4 receptor and has a stimulating action on a serotonin-like receptor. Therefore, the compound of the present invention has activating gastrointestinal motor functions, and thus is effective for the improvement of gastrointestinal conditions such as heartburn, anorexia, bowel pain or abdominal distension accompanied by chronic gastritis or postoperative gastroparesis, and further for the treatment of gastroesophagal reflux, intestinal pseudo-obstruction or constipation.

With respect to toxicity of Compound (1) represented by Formula (I) which is an effective ingredient of the pharmaceutical composition of the present invention, as a result of the toxicity examination of mouse single administration (acute toxicity), the LD value is more than 500 mg/kg by oral administration.

A dose of the compound of Formula (I) varies depending upon conditions, but a daily dose for adult is usually from 0.1 to 100 mg/human for oral administration, from 0.01 to 20 mg/human for intravenous administration, and may be given at once or by dividing into 2 to 4 times.

The pharmaceutical composition of the present invention can be prepared for use in the forms of solid preparations (e.g. tablets, pills, capsules or granules), injections, solutions, emulsions or suppositories.

The above-mentioned pharmaceutical preparations can be made in a conventional pharmaceutical technique, if desired, by using conventional additives such as adjuvants, stabilizers, emulsifiers or diluents.

EXPERIMENTS

Compound (1) of the present invention is hereinafter illustrated in more detail with respect to the stimulating action on a serotonin 4 receptor and the activating action on gastrointestinal motor functions.

Experiment 1

Stimulating Action Test on Serotonin 4 Receptor Test Drugs

Test Drug 1: Compound 1 of the present invention

Test Drug 2: The compound described in Japanese Patent Kokai No. 3-197462 represented by the following formula:

Test Drug 3: The compound described in Japanese Patent Kokai No. 4-226980 represented by the following formula:

Test Method

Twitch responses were examined in longitudinal muscle strips of guinea pig according to a modification of the method described in The Journal of Pharmacology and Experimental Therapeutics, vol. 252, page 1378, 1990.

From Hartley guinea pigs, a section of ileum 25 cm in length and proximal to the ileocecal junction was removed. The longitudinal muscle strips obtained from two segments of ileum about 4 cm each in length were used for this test. The longitudinal muscle strips were suspended in Kreb's solution at 32° to 34° C. and bubbled with 95% $O_2$ and 5% $CO_2$ under a load of about 0.8 g. The responses were recorded under an electrical stimulation of 0.2 Hz, 1 msec pulse duration, using force displacement transducers. The longitudinal muscle strips were allowed to stand at supramaximal voltage for about an hour, and thereby were stable. After it was confirmed that the twitch responses were enhanced by $10^{-8}M$ 5-HT, each test drug was examined on its activity for twitch responses. The test was carried out by exposing the strips to cumulative additions of the test drug at least at 45 minute intervals.

Results are shown in Table 1.

TABLE 1

| Test drug | $ED_{50}(nM)$ |
|---|---|
| 1 | 21.3 |
| 2 | >3000 |
| 3 | >3000 |

Experiment 2

Action on Gastrointestinal Motor in Dogs

Test Method

The test was carried out by a modification of the method described in Gastroenterologia Japonica, vol. 12, page 275, 1977.

Beagle dogs of both sexes weighing 9 to 15 kg were anesthetized with sodium pentobarbital and strain gauge force transducers were sutured on 5 portions, i.e. for determining antral, duodenum, jejunal, ileal and colonel motor responses. A cannula for administering a drug was mounted persistently into the jugular vein. After recovery of the surgery, motor responses of the dog under no-anesthesia without restriction at those portions on the gastrointestinal tract in both during a fasting period and after feeding were determined in the conscious drugs.

The compound of the present invention was administered after dissolving in saline aqueous solution.

The motor index is shown in terms of a proportion (%) of a mean value calculated for 15 minutes to a value prior to administration (0 minute). The value for 0 minute was made a mean value for 30 minutes prior to the administration.

Results

The compound of the present invention showed acceleration on the motor action on the gastrointestinal tract by intravenous and oral administrations, both during the fasting period and after feeding. On the other hand, no influence was confirmed when the vehicle alone was given.

Tables 2 and 3 show the activity of the compound of the present invention in doses of 0.3 mg/kg for intravenous route and 1 mg/kg for oral route, respectively, on the gastric motor action after feeding.

TABLE 2

Intravenous Administration

| Time after administration (min.) | Motility Index (%) |
|---|---|
| 0 | 100 |
| 15 | 247.8* |
| 30 | 219.8** |
| 45 | 178.8** |
| 60 | 162.3** |
| 75 | 181.0*** |
| 90 | 166.7 |
| 105 | 150.1 |
| 120 | 123.5 |

*$p < 0.05$
**$p < 0.01$
***$p < 0.001$
N = 3

TABLE 3

Oral Administration

| Time after administration (min.) | Motility Index (%) |
|---|---|
| 0 | 100 |
| 15 | 179.5 |
| 30 | 238.6 |
| 45 | 295.0 |
| 60 | 238.8 |
| 75 | 252.3 |
| 90 | 193.9 |
| 105 | 251.7 |
| 120 | 257.8 |
| 135 | 220.6* |
| 150 | 158.1 |
| 165 | 201.9 |
| 180 | 188.9* |

*$p < 0.05$,
N = 3

Experiment 3
Action on Gastric Emptying in Rats
Test Method

The test was carried out by a modification of the method described in British Journal of Pharmacology, vol. 91, page 263, 1987.

Male wistar rats weighing 170 to 220 g were used after fasting for 24 hours.

Clonidine hydrochloride of 30 μg/kg was administered subcutaneously, and after 30 minutes the compound of the present invention was administered subcutaneously. After 30 minutes 1 ml of glass balls (500 mg/ml) was administered orally. After 30 minutes the glass balls remained in the stomach were recovered and weighed to determine the rate [residual rate in stomach (%)] to the residual amount in the stomach of the clonidine hydrochloride-treated animal.

The compound of the present invention was administered after dissolving in saline aqueous solution.

Results

The compound of the present invention inhibited dose-dependent accelerating action on gastric emptying in subcutaneous administration, as shown in Table 4.

TABLE 4

| Dose (mg/kg) | No. of Case | Residual rate in Stomach (%) |
|---|---|---|
| 0.03 | 5 | 59.2 |
| 0.1 | 5 | 50.4 |
| 0.3 | 6 | 38.7 |
| 1.0 | 6 | 40.0 |

EXAMPLES

The present invention is illustrated in more detail by the following preparation examples and examples.

Preparation Example 1

Preparation of endo-(8-methyl-8-azabicyclo-[3.2.1]oct-3-yl) 1-isopropyl-2(1H)-quinolone-3- carboxylate 1) Ethyl 2(1H)-quinolone-3-carboxylate To a solution of 45 g of diethyl 2-nitrobenzylidenemalonate (J. Org. Chem., page 3462, 1960) in 700 ml of acetic acid was added 53 g of iron powders in several portions while keeping at 80° C., followed by stirring for 2 hours.

The temperature was reverted to room temperature, followed by filtration through celite. The filtrate was concentrated under reduced pressure, and the resulting oily substance was purified by silica gel column chromatography (chloroform–methanol=10:1) to give 21.3 g of ethyl 2(1H)-quinolone-3-carboxylate. m.p. 160°–163.2° C. (ethyl acetate)

2) Ethyl 1-isopropyl-2(1H)-quinolone-3-carboxylate

To a solution of 4.45 g of sodium hydride in 100 ml of DMF was added 20 g of ethyl 2(1H)-quinolone-3-carboxylate, and then 31.5 g of isopropyl iodide was added thereto, followed by stirring at 70° C. for 8 hours. After evaporation of DMF under reduced pressure, the residue was taken into water and extracted with ethyl acetate. The organic layer was washed with water and a saturated aqueous sodium chloride solution and then dried over anhydrous sodium sulfate.

The solvent was evaporated under reduced pressure, and the resulting oily substance was purified by silica gel column chromatography (ethyl acetate:n-hexane=4:1) to give 1.55 g of ethyl 1-isopropyl-2(1H)-quinolone-3-carboxylate. m.p. 54°–57° C. (ethyl acetate)

3) 1-Isopropyl-2(1H)-quinolone-3-carboxylic acid

A solution of 1.55 g of ethyl 1-isopropyl-2(1H)-quinolone-3-carboxylate and 0.28 g of sodium hydroxide in a solvent mixture of 10 ml of ethanol and 2 ml of water was stirred at room temperature overnight. The solvent was evaporated under reduced pressure, and after addition of dil. hydrochloric acid, the precipitated solid was collected by filtration, washed with water and dried to give 1.22 g of 1-isopropyl-2(1H)-quinolone-3-carboxylic acid. m.p. 168°–169° C. (ethyl acetate)

4) Endo-(8-methyl-8-azabicyclo[3.2.1]oct-3-yl) 1-isopropyl-2(1H)-quinolone-3-carboxylate To a suspension of 1 g of 1-isopropyl-2-(1H)-quinolone-3-carboxylic acid in 10 ml of tetrahydrofuran was added 1.6 ml of thionyl chloride, followed by stirring at 80° C. for an hour. The solvent was evaporated under reduced pressure, and 10 ml of tetrahydrofuran was added thereto, followed by further evaporation under reduced pressure. To the residue was added 20 ml of tetrahydrofuran to give a solution of an acid chloride in tetrahydrofuran.

To a solution of 740 mg of tropine in 10 ml of tetrahydrofuran was added dropwise 3.5 ml of n-butyl lithium (1.56M, n-hexane solution) under ice-cooling, followed by stirring for 30 minutes. To the solution was added dropwise the solution of the acid chloride in tetrahydrofuran previously prepared, followed by stirring at room temperature for a day. After evaporation of the solvent, 2N hydrochloric acid was added, followed by washing with ethyl acetate. The aqueous layer was made basic with sodium bicarbonate and extracted with chloroform. The chloroform layer was dried over anhydrous sodium sulfate. After evaporation of the solvent, the resulting residue was purified by silica gel column chromatography (chloroform:methanol=20:1) to give 530 mg of endo-(8-methyl-8-azabicyclo[3.2.1]oct-3-yl) 1-isopropyl-2(1H)-quinolone-3-carboxylate. MS(m/z): 354 ($M^{3O}$), 310, 269, 172, 124 IR$\upsilon$(cm$^{-1}$, Neat): 2937, 1733, 1652, 1211, 1034, 754.

NMR(ppm, CDCl$_3$): 1.66(6H, d, J=6.9Hz), 1.88(1H, s), 1.92(1H, s), 2.00~2.30(6H, m), 2.32(3H, s), 3.17(2H, s), 5.27(1H, t, J=5.4 Hz), 5.30~5.70(1H, bs), 7.19~7.30(1H, m), 7.55~7.68(3H, m), 8.22(1H, s).

Preparation Example 2

Endo-(8-methyl-8-azabicyclo[3.2.1]oct-3-yl) 1-isopropyl-2(1H)-quinolone-3-carboxylate hydrochloride To a solution of 510 mg of endo-(8-methyl-8-azabicyclo[3.2.1]oct-3-yl) 1-isopropyl-2(1H)-quinolone-3- carboxylate in 2 ml of ethanol was made acidic with conc. hydrochloric acid. After evaporation of the solvent, recrystallization from ethanol gave 340 mg of endo-(8-methyl-8-azabicyclo[3.2.1]oct-3-yl) 1-isopropyl-2(1H)-quinolone-3-carboxylate hydrochloride. m.p. 252.5°–253.5° C. (ethanol)

Preparation Example 3

Endo-(8-methyl-8-azabicyclo[3.2.1]oct-3-yl) 1-isopropyl-2(1H)-quinolone-3-carboxylate 1) 2-Isopropylaminobenzaldehyde To a solution of 9.6 g of 2-isopropylaminobenzyl alcohol in 200 ml of dioxane was added 13.2 g of 2,3-dichloro-5,6-dicyano-1,4-benzoquinone (DDQ) in several portions, followed by stirring for an hour. The solvent was evaporated, the reaction solution was concentrated, and methylene chloride was added thereto, followed by filtration. The filtrate was concentrated, and the resulting oily substance was purified by silica gel column chromatography (n-hexane:ethyl acetate=5:1) to give 7.6 g of 2-isopropylaminobenzaldehyde.

NMR(ppm, CDCl$_3$): 1.27(6H, d, J=6.4Hz), 3.67~3.83 (1H, m), 6.59–6.73(2H, m), 7.31~7.43(1H, m), 7.44(1H, dd, J=7.6, 1.4Hz), 8.26(1H, s), 9.79(1H, s)

2) Ethyl 1-isopropyl-2(1H)-quinolone-3-carboxylate

A solution of 7.5 g of 2-isopropylaminobenzaldehyde, 11.0 g of diethyl malonate and 11.6 g of sodium bicarbonate in 800 ml of acetic anhydride was stirred under heating at 100° C. for 15 hours. After evaporation of the solvent under reduced pressure, water was added, followed by extraction with ethyl acetate. The organic layer was washed with water and a saturated aqueous sodium bicarbonate solution and dried over anhydrous sodium sulfate. The solvent was evaporated under reduced pressure, and the resulting oily substance was purified by silica gel column chromatography (n-hexane:ethyl acetate=4:1) to give 7.3 g of ethyl 1-isopropyl-2(1H)-quinolone-3-carboxylate.

3) Endo-(8-methyl-8-azabicyclo[3.2.1]oct-3-yl) 1-isopropyl-2(1H)-quinolone-3-carboxylate Following the same procedures as those of Preparation Example 1-4) and 1-5), endo-(8-methyl-8- azabicyclo [3.2.1]oct-3-yl) 1-isopropyl-2(1H)-quinolone-3- carboxylate was obtained.

Pharmaceutical Composition Example

Preparation of tablets

Formulation (per tablet)

| Compound (1) | 2 mg |
|---|---|
| Lactose | 19 mg |
| Potato starch | 20 mg |
| Crystalline cellulose | 28 mg |
| Carboxymethyl cellulose | 20 mg |
| Hydroxymethyl cellulose | 10 mg |
| Magnesium stearate | 1 mg |

Preparation Method 20 g of Compound (1), 190 g of lactose, 200 g of potato starch, 280 g of crystalline cellulose, 200 g of carboxymethyl cellulose and 100 g of hydroxymethyl cellulose were blended each other, and ground by a crusher. The powders were put into a mixing granulation machine, and a small quantity of water was added to the powder for granulation, followed by drying by a fluidized bed dryer. To the granules was added 10 g of magnesium stearate, followed by tableting by a tableting machine to give tablets each 100 mg in weight and 6 mm diameter, containing 2 mg of Compound (1).

Industrial Utilization

Compound (1) of the present invention acts on a serotonin 4 receptor and thereby have a serotonin-like receptor stimulating activity. More specifically, Compound (1) has an action on activating gastrointestinal motor functions, and thus is effective for the improvement of gastrointestinal conditions such as heartburn, anorexia, bowel pain or abdominal distension accompanied by chronic gastritis or postoperative gastroparesis, and further for the treatment of gastro-esophagal reflux, intestinal pseudo-obstruction or constipation.

We claim:

1. Endo-(8-methyl-8-azabicyclo[3.2.1]oct-3-yl) 1-isopropyl-2(1H)-quinolone-3-carboxylate represented by Formula (I):

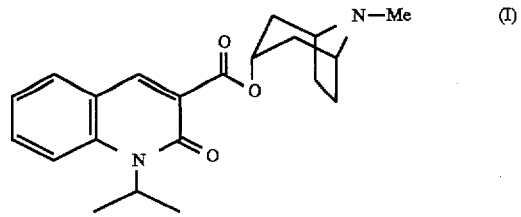

or a pharmaceutically acceptable salt thereof.

2. The compound or a pharmaceutically acceptable salt thereof according to claim 1 for use as an effective ingredient of a pharmaceutical composition.

3. A pharmaceutical composition for stimulating a serotonin 4 receptor comprising as an effective ingredient the compound or a pharmaceutically acceptable salt thereof according to claim 1.

4. A method for stimulating a serotonin 4 receptor which comprises administering a pharmacologically effective amount of the compound or a pharmaceutically acceptable salt thereof according to claim 1 to a mammal.

5. The method of claim 4 wherein said mammal is a human.

6. A method of treating a gastrointestinal condition which comprises administering to a patient in need of such treatment, a therapeutically effective amount of the compound or a pharmaceutically acceptable salt thereof according to claim 1, said gastrointestinal condition being selected from the group consisting of heartburn, anorexia, bowel pain accompanied by chronic gastritis or postoperative gastroparesis, abdominal distention accompanied by chronic gastritis or postoperative gastroparesis, gastro-esophagal reflux, intestinal pseudo-obstruction and constipation.

\* \* \* \* \*